United States Patent
Krishnaiah et al.

(10) Patent No.: US 12,304,887 B2
(45) Date of Patent: May 20, 2025

(54) RECOVERY OF LIGHT OLEFINS FROM DRY HYDROCARBON GAS FROM REFINERY AND PETROCHEMICAL PRODUCTION PROCESSES FOR PRODUCTION OF ALKYLATE

(71) Applicants: Gautham Krishnaiah, Houston, TX (US); Brian Heasley, Cypress, TX (US); John Lewis Webb, Jr., Richmond, TX (US); Rahul Radhakrishna Pillai, Manvel, TX (US); Vijender K. Verma, Richmond, TX (US); Narinder Singh Duggal, Haryana (IN)

(72) Inventors: Gautham Krishnaiah, Houston, TX (US); Brian Heasley, Cypress, TX (US); John Lewis Webb, Jr., Richmond, TX (US); Rahul Radhakrishna Pillai, Manvel, TX (US); Vijender K. Verma, Richmond, TX (US); Narinder Singh Duggal, Haryana (IN)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 18/450,266

(22) Filed: Aug. 15, 2023

(65) Prior Publication Data
US 2023/0391691 A1    Dec. 7, 2023

Related U.S. Application Data

(62) Division of application No. 17/130,260, filed on Dec. 22, 2020, now Pat. No. 11,905,241.

(51) Int. Cl.
C07C 7/11        (2006.01)
B01D 53/14       (2006.01)
(Continued)

(52) U.S. Cl.
CPC ............ *C07C 7/11* (2013.01); *B01D 53/1406* (2013.01); *B01D 53/1468* (2013.01);
(Continued)

(58) Field of Classification Search
None
See application file for complete search history.

(56) References Cited

U.S. PATENT DOCUMENTS 2,511,758 A * 6/1950 Weinrich ................. C07C 2/62
568/893
2,970,177 A * 1/1961 Cobb, Jr. ............... C07C 7/005
95/223
(Continued)

OTHER PUBLICATIONS

European Patent Office; Supplementary European Search Report dated Jan. 23, 2025 for European Application No. EP21911933; 3 pages.

*Primary Examiner* — Tam M Nguyen
(74) *Attorney, Agent, or Firm* — Gary M. Machetta

(57) ABSTRACT

Methods and systems for treating an olefin-containing stream are disclosed. The disclosed methods and systems are particularly suitable for treating an off-gas stream in a refining or petrochemical process, such as from a fluid catalytic cracker (FCC), coker, steam cracker, and the like. The stream is treated in an absorber column to reject lighter stream components and to absorb ethylene and/or propylene into a solvent. The solvent is typically isobutane. The enriched solvent stream from the absorber column is fed to an alkylation reactor, which reacts the dissolved olefin with the isobutane solvent to produce an alkylate product.

6 Claims, 1 Drawing Sheet

(51) Int. Cl.
*B01D 53/18* (2006.01)
*B01J 8/02* (2006.01)
*C07C 2/12* (2006.01)
*C07C 7/00* (2006.01)
*C07C 7/09* (2006.01)

(52) U.S. Cl.
CPC ..... *B01D 53/1475* (2013.01); *B01D 53/1487* (2013.01); *B01D 53/1493* (2013.01); *B01D 53/18* (2013.01); *B01J 8/02* (2013.01); *C07C 2/12* (2013.01); *C07C 7/005* (2013.01); *C07C 7/09* (2013.01); *B01D 2252/10* (2013.01); *B01D 2252/204* (2013.01); *B01D 2252/205* (2013.01)

(56) References Cited

U.S. PATENT DOCUMENTS 3,564,073 A * 2/1971 Goldsby .................. C07C 2/62
585/311
3,925,500 A 12/1975 Wentzheimer

* cited by examiner

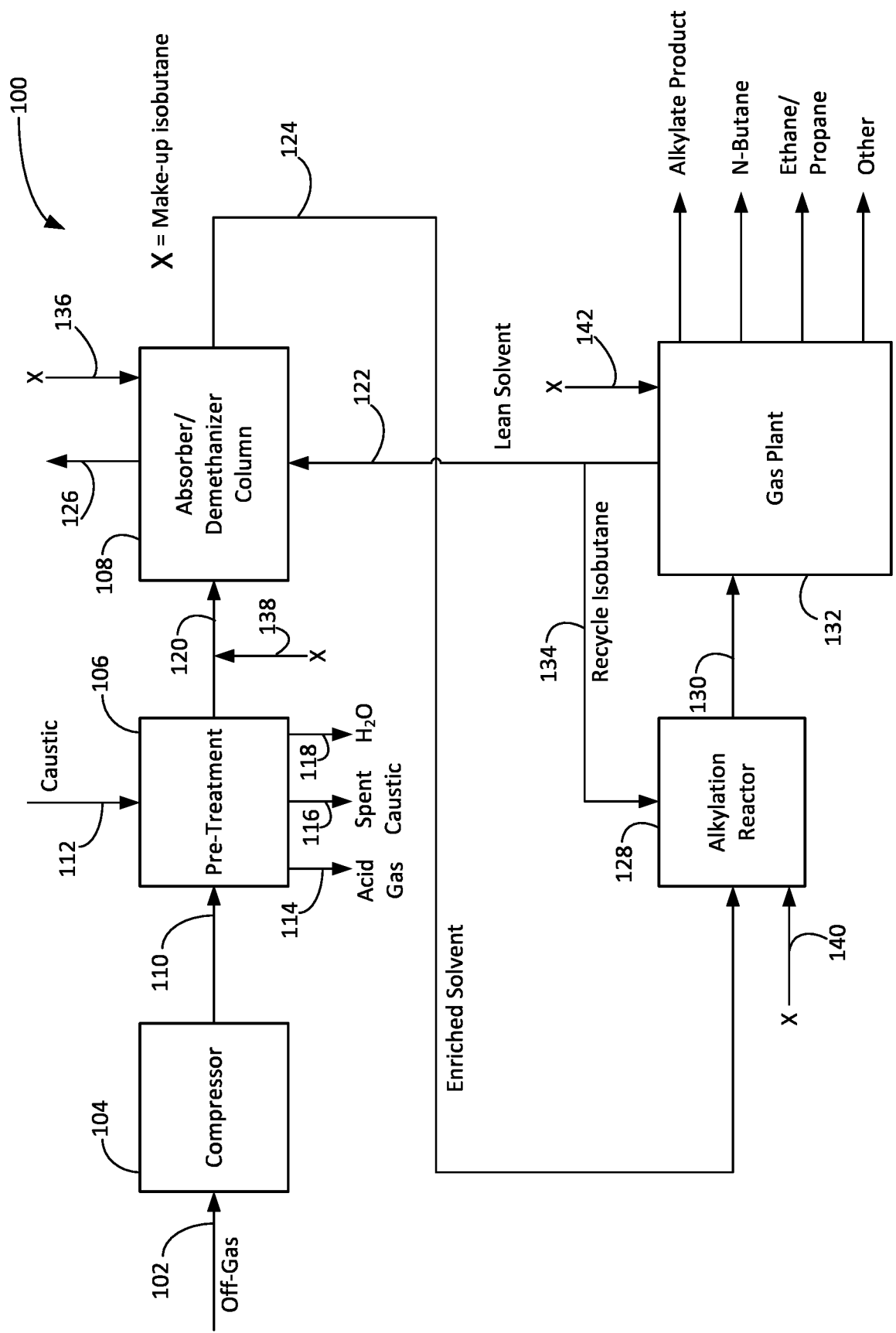

RECOVERY OF LIGHT OLEFINS FROM DRY HYDROCARBON GAS FROM REFINERY AND PETROCHEMICAL PRODUCTION PROCESSES FOR PRODUCTION OF ALKYLATE

CROSS-REFERENCE TO RELATED APPLICATION

This application is a divisional of U.S. application Ser. No. 17/130,260, filed Dec. 22, 2020, now U.S. Pat. No. 11,905,241, the contents of which are hereby incorporated by reference in its entirety.

FIELD OF THE INVENTION

This application relates to methods and systems for recovering light olefins from refinery and petrochemical production processes, and more particularly, for absorbing light olefins into a feed stream for an alkylation reaction.

INTRODUCTION

Petrochemical and refinery operations often involve processes that convert (i.e., "crack") high-boiling, high-molecular weight hydrocarbons into an array of lighter, lower-boiling, and more valuable products. For example, fluid catalytic cracking (FCC) is widely used in refineries to convert heavy petroleum components into high-value fuels. FCC and other cracking processes make a range of products, from light gases to heavy fuel oil. Steps and processes within the refinery are used to isolate the various FCC products based on their boiling ranges, yielding products such as petroleum naphtha, gasoline, diesel fuel, heating oil, jet fuel, and fuel oils.

The stream from the FCC unit that contains the lightest components is referred to as off-gas. The off-gas stream typically contains ethane, ethylene, methane, and hydrogen, as well as impurities, such as carbon monoxide, carbon dioxide, and hydrogen sulfide. The off-gas stream is considered as having low value because the only valuable component is the ethylene and it is generally expensive to extract the ethylene from the off-gas stream. Thus, refiners typically send the off-gas stream to a fuel gas system, so that it can be burned to produce heat for processes within the refinery, thereby recovering some value from the stream. However, it would be beneficial if the ethylene contained in the off-gas stream could be used for a higher purpose than being burned as fuel gas.

SUMMARY

Disclosed herein is a method of treating an olefin-containing stream, wherein the olefin-containing stream comprises: one or more olefins selected from the group consisting of ethylene and propylene, and one or more light components selected from the group consisting of hydrogen ($H_2$), carbon monoxide (CO), and methane, the method comprising: providing the olefin-containing stream to an absorber column, separating the one or more olefins from the one or more light components by contacting the olefin-containing stream with a solvent in the absorber column to absorb at least a portion of the one or more olefins in the solvent to provide an olefin-enriched solvent stream, wherein the solvent is an alkylation precursor, providing the olefin-enriched solvent stream to an alkylation reactor, and reacting the one or more olefins with the solvent in the alkylation reactor to produce an alkylate. According to some embodiments, the solvent is isobutane. According to some embodiments, the olefin-containing stream is an off-gas from a fluid catalytic cracking (FCC) process. According to some embodiments, the olefin containing stream further comprises one or more contaminants selected from the group consisting of carbon dioxide, water, and hydrogen sulfide, and wherein the method further comprises pre-treating the olefin-containing stream to remove one or more of the contaminants. According to some embodiments, the pre-treating comprises scrubbing the olefin-containing stream with an amine. According to some embodiments, the pre-treating comprises contacting the olefin-containing stream with a caustic material. According to some embodiments, reacting the one or more olefins with the solvent in the alkylation reactor to produce an alkylate comprises dimerizing the one or more olefins to produce a dimer and reacting the dimer with the solvent to yield the alkylate. According to some embodiments, the alkylation reactor comprises a fixed catalyst bed comprising a solid acid alkylation catalyst. According to some embodiments, reacting the one or more olefins with the solvent in the alkylation reactor to produce an alkylate comprises generating an alkylation reactor effluent stream comprising the alkylate. According to some embodiments, the method further comprises: providing the alkylation reactor effluent stream to one or more fractionating columns, recovering lean solvent from the one or more fractionating columns, and recovering enriched alkylate product from the one or more fractionating columns. According to some embodiments, the method further comprises recycling at least a portion of the lean solvent to the absorber column. According to some embodiments, the method further comprises recycling at least a portion of the lean solvent to the alkylation reactor.

Also disclosed herein is a system for treating an olefin-containing stream, wherein the olefin-containing stream comprises: one or more olefins selected from the group consisting of ethylene and propylene, and one or more light components selected from the group consisting of hydrogen ($H_2$), carbon monoxide (CO), and methane, the system comprising: an absorber column and an alkylation reactor, wherein the absorber column is configured to separate the one or more olefins from the one or more light components by contacting the olefin-containing stream with a solvent to absorb at least a portion of the one or more olefins into the solvent to provide an olefin-enriched solvent stream, wherein the solvent is an alkylation precursor, and wherein the alkylation reactor is configured to receive the olefin-enriched solvent stream and react the one or more olefins with the solvent to produce an alkylate. According to some embodiments, the solvent is isobutane. According to some embodiments, the olefin-containing stream is an off-gas from a fluid catalytic cracking (FCC) process. According to some embodiments, the system further comprises an amine scrubber upstream of the absorber column, wherein the amine scrubber is configured to remove one or more contaminants selected from the group consisting of carbon dioxide and hydrogen sulfide from the olefin-containing stream. According to some embodiments, the system further comprises a caustic contact vessel upstream of the absorber column, wherein the caustic contact vessel is configured to contact the olefin-containing stream with a caustic material to remove one or more contaminants selected from the group consisting of carbon dioxide and hydrogen sulfide from the olefin-containing stream. According to some embodiments, the alkylation reactor comprises a fixed catalyst bed comprising a solid acid alkylation catalyst. According to some embodiments, the alkylation reactor is configured to provide an alkylation reactor effluent stream comprising the alkylate to one or more fractionating columns, wherein the one or more fractionating columns are configured to separate the alkylation reactor effluent stream into a lean solvent stream and an enriched alkylate product stream. According to some embodiments, the system is configured to recycle the lean solvent stream to one or more of the absorber column and the alkylation reactor.

BRIEF DESCRIPTION OF THE DRAWINGS

FIG. 1 shows a system for treating an olefin-containing stream.

DETAILED DESCRIPTION

This disclosure provides methods and systems for absorbing C2 and/or C3 olefins (i.e., ethylene and/or propylene) from an off-gas stream of a refinery/petrochemical process. Generally, C2+ hydrocarbons (including small amounts of C4/C5) are absorbed while C1 and hydrogen are rejected. The disclosed methods and systems are primarily discussed in the context of treating an FCC off-gas. But it should be appreciated that the methods and systems can be used to treat off-gases (and other C2/C3 olefin-containing streams) generated by other processes, such as cokers, ethylene and propylene recovery units, steam crackers, and the like. Generally, the methods and systems can be used with any ethylene and/or propylene-containing stream.

The disclosed methods and systems involve absorbing the C2 and/or C3 olefins into a feed stream, which feed stream is then provided to an alkylation reactor to produce an alkylate product. Alkylate is the cleanest gasoline blending stream produced in refineries and is an ideal clean fuel component because it has a high octane rating, low vapor pressure, and low toxicity. Alkylate has been blended into gasoline for decades to improve the octane rating and, thus, the antiknock properties of gasoline. In addition, strict state and federal limitations on the formulation and physical properties of gasoline make alkylate one of the most important and valuable blend-stocks of the gasoline pool. The disclosed methods and systems provide a substantial increase in value for treating an off-gas stream by converting the C2 and/or C3 olefin in the off-gas stream to a valuable alkylate product, as opposed to sending the olefin to the refinery's fuel gas system.

FIG. 1 illustrates a system 100 for absorbing C2/C3 olefins from a stream and providing them as part of a feed stream for an alkylation reaction. In the illustrated system 100, an olefin-containing stream is provided to the system via line 102. In the illustrated system, the olefin-containing stream is an off-gas stream, for example, from an FCC unit. As mentioned above, such an off-gas stream may comprise ethylene and/or propylene, ethane, methane, and hydrogen, as well as impurities, such as carbon monoxide, carbon dioxide, and hydrogen sulfide. A typical off-gas stream may have a pressure of about 120 psig, for example.

In the illustrated system 100, the off-gas stream is pressurized in a compressor 104 to liquify some of the components of the stream. For example, the off-gas stream may be pressurized to a pressure of about 180 to about 250 psig. The discharge pressure of the compressor 104 can be set so that the stream can pass through the pre-treatment section 106 and into the absorber/demethanizer column (A/D column) 108, which operates at a pressure of about 135 psig, as described below. According to one embodiment, the discharge pressure of the compressor 104 can be set to about 230 psig.

The compressed stream 110 may be provided to a pre-treatment section 106. The purpose of the pre-treatment section 106 is to remove various contaminants from the stream and condition the stream for the downstream A/D column 108. According to some embodiments, the pre-treatment section 106 may include an amine system for bulk carbon dioxide ($CO_2$) and/or $H_2S$ removal, a caustic wash for final $CO_2/H_2S$ removal, and/or dryers for removing moisture. Such equipment and processes are well known to those of ordinary skill in the art. For example, an amine scrubbing system may involve contacting the compressed olefin-containing stream with an amine, such as monoethanolamine, diethanolamine, methyldiethanolamine, or diglycolamine to absorb $CO_2$ and/or $H_2S$ from the olefin-containing stream. A typical amine gas treating process includes an absorber unit and a regenerator unit as well as accessory equipment. In the absorber, the downflowing amine solution absorbs $H_2S$ and $CO_2$ from the upflowing olefin-containing stream to produce a sweetened olefin-containing stream (i.e., the olefin-containing stream free of $H_2S$ and $CO_2$) as a product and an amine solution rich in the absorbed acid gases ($H_2S$ and $CO_2$). The resultant "rich" amine is then routed into the regenerator (a stripper with a reboiler) to produce regenerated or "lean" amine that is recycled for reuse in the absorber. The stripped overhead gas stream from the regenerator is concentrated $H_2S$ and $CO_2$ may be routed for acid gas treatment. Following the amine scrubber, the olefin-containing stream may be contacted with caustic in a vessel for further sweetening. The stream may be dried by contacting it with an absorbent bed comprising molecular sieve material. In the illustrated embodiment, caustic material, such as sodium hydroxide or other caustic material known in the art is provided to the pre-treatment section 106 via line 112. Acid gas, spent caustic, and water exit the pre-treatment section 106 via lines 114, 116, and 118, respectively. It should be appreciated that various different pre-treatment processes may be performed to purify the off-gas stream depending on the particular implementation and components of the off-gas stream. According to some embodiments, the pre-treated off-gas stream may be cooled prior to providing it to the A/D column 108. For example, the compressed off-gas stream may be cooled to a temperature of about 35° F.

In the illustrated embodiment, the pre-treated off-gas stream is provided to the A/D column 108 via line 120. The pre-treated off-gas stream in line 120 may comprise ethylene and/or propylene and other components, such as hydrogen ($H_2$), carbon monoxide (CO), methane, ethane, propane, n- and/or i-butane, butenes, pentenes, pentanes, and the like. The specific composition of the pre-treated off-gas stream in line 120 will depend upon the composition of the original stream (i.e., stream 102) and the operating parameters of the upstream equipment, such as the compressor 104 and the pre-treatment section 106. Ideally, it is desirable that the pre-treated off-gas stream in line 120 be enriched in olefins (i.e., ethylene and/or propylene).

The A/D column 108 is an absorber column that serves the dual purposes of 1) absorbing the olefins (i.e., ethylene and/or propylene) from the off-gas stream into a solvent while rejecting lighter components, such as $H_2$, CO, and methane, and 2) providing the olefins to an alkylation reactor as a feed stream that is specifically suitable for the alkylation reaction. As mentioned above, heavier components (such as C2+ paraffins) will also be absorbed. In the A/D column, the pre-treated off-gas stream is contacted with a solvent that is also a reactant in the downstream alkylation reactor. In other words, the solvent is itself an alkylation precursor. According to some embodiments, the solvent is isobutane, though it could be other compounds, such as isopentane. In the system 100, lean isobutane is provided to the A/D column 108 via line 122. The isobutane contacts the pre-treated off-gas in the A/D column, yielding an enriched solvent stream 124 that is enriched in olefins and heavier components from the off-gas, which is provided to the alkylation reactor 128, as described below. Unabsorbed lighter components, such as $H_2$, CO, and the like exit the A/D column via line 126 and may be subjected to further processing, such as pressure swing adsorption (PSA).

According to some embodiments, the A/D column 108 may comprise a single column, operating at a pressure, to contact the olefin(s) with isobutane solvent. Parameters that may be varied to improve olefin absorption include the inclusion of trays, the number of trays, the range of operating temperatures and pressures, and the solvent-to-olefin ratio. According to some embodiments, the A/D column has around 20 theoretical stages (which can be conventional trays or an equivalent amount of packing) with a solvent to feed ratio of 2.45 wt/wt. According to some embodiments, the solvent can be cooled using an overhead condenser and fed to the top of the tower as reflux. According to some embodiments, the temperature profile can be about −30° F. at the top stage and about 0° F. at the bottom stage, for example. According to some embodiments, the pre-treated off-gas feed can enter the bottom of the tower with a vapor fraction of around 0.80. The A/D column may or may not include a reboiler. According to some embodiments, the net liquid bottom stream 124 may be sent to a feed/effluent exchanger and/or solvent/effluent exchange (not shown) to heat the stream (for example, to a temperature of about 60° C.) before sending it to the alkylation reactor. According to some embodiments, the overhead stream can be partially condensed and sent to a reflux drum (not shown). Non-condensables may be vented from the drum as a net overhead vapor stream 126 and can be sent to a PSA unit for further purification. That stream is predominately molecules that are lighter than ethylene. According to some embodiments, the target is for ~90% ethylene recovery from the A/D column 108.

The enriched solvent stream 124 is provided to one or more alkylation reactors 128. As mentioned above, the enriched solvent stream is enriched with ethylene and/or propylene and heavier components. The solvent is typically isobutane, which serves both as a solvent and as a reactant in the alkylation reaction. The alkylation reactor converts the absorbed olefin and isobutane to an alkylate. U.S. Pat. No. 9,079,815 describes examples of converting ethylene and isobutane to alkylate. According to some embodiments, the alkylation reactor uses solid acid alkylation technology to convert the olefin and isobutane to alkylate. A particularly suitable alkylation reactor technology is KBR's K-SAAT™ alkylation technology (KBR, Houston, TX). This alkylation process uses a fixed bed catalyst, which is typically a zeolite material supporting non-precious metals. An example of a suitable catalyst is KBR's ExSact™ catalyst (KBR, Houston, TX). In the case of conversion of ethylene to alkylate, first, two ethylene molecules dimerize, i.e., react with each other to form butylene. The butylene then reacts with isobutane to form the alkylate, isooctane. The amount of isobutane in the system can be controlled, as explained below, to push the reaction equilibrium toward product.

Control of the stoichiometry of reactants (i.e., olefins and isobutane) provided to the alkylation reactor(s) 128 is based on analysis of the components of the stream 124. For example, according to some embodiments, it is desirable to have a molar ratio of about 10:1 isobutane to propylene and to have a molar ratio of about 5:1 isobutane to ethylene. Thus, the feed stream composition can be determined and the amount of isobutane in the system can be adjusted (as described in more detail below) to maintain the correct stoichiometry in the alkylation reactor 128.

The effluent stream 130 from the alkylation reactor(s) 128 may comprise, for example, about 10-12% alkylate product with the balance being primarily isobutane. The reactor effluent stream 130 may be provided to further purification processes, collectively shown in FIG. 1 as a gas plant 132. The gas plant 132 may comprise one or more fractionating columns, for example. According to some embodiments, the gas plant includes a fractionating column configured to recover lean isobutane and recycle it (or a portion of it) to the A/D column via line 122. According to some embodiments, a portion of the recovered lean isobutane may be recycled to the alkylation reactor(s) via line 134. According to some embodiments, n-butane may be taken as a side stream of that fractionating column. The gas plant may include other fractionating columns, for example, for separating other components, such as ethane, propane, and other off-gas products.

As mentioned above, a portion of the recovered lean solvent (isobutane) may be recycled to the alkylation reactor 128 via line 134. This can be helpful for several reasons. First, according to some embodiments, it is desirable to recycle as little isobutane as possible to the A/D column 108 because using high volumes of isobutane necessitates a larger column and uses more energy. Also, as mentioned above, the equilibrium of the alkylation reaction can be controlled by controlling the amount of isobutane provided to the alkylation reactor. Thus, the isobutane recycle stream 134 provides a lever for controlling the alkylation reaction.

Make-up isobutane can be provided to the system 100 at various points, as shown in FIG. 1. For example, make-up isobutane may be provided to the A/D column 108 via line 136. According to some embodiments, make-up isobutane may be mixed with the pre-treated off-gas in line 120 (via line 138) before the pre-treated off-gas enters the A/D column 108. For example, a static mixer, bubbler, or the like could be used to precontact the pre-treated off-gas with make-up isobutane before providing the mixture to the A/D column. Make-up isobutane may be added directly to the alkylation reactor 128 via line 140 and/or to a component of the gas plant 132 via line 142.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:
1. A system for treating an olefin-containing stream, wherein the olefin-containing stream comprises:
one or more olefins selected from the group consisting of ethylene and propylene, and one or more light components selected from the group consisting of hydrogen (H2), carbon monoxide (CO), and methane, the system comprising:

an absorber column comprising a hydrocarbon solvent and is configured to separate the one or more olefins from the one or more light components by contacting the olefin-containing stream with the hydrocarbon solvent at a pressure of about 135 psi and at a temperature ranging from −30° F. at the top of the column to 0° F. at the bottom of the column to absorb at least a portion of the one or more olefins into the solvent to provide an olefin-enriched solvent stream, wherein the solvent is an alkylation precursor;

an alkylation reactor is configured to receive the olefin-enriched solvent stream and react the one or more olefins with the solvent to produce an alkylate;

one or more fractionating columns configured to receive an alkylation reactor effluent stream comprising the alkylate, the one or more fractionating columns configured to separate the alkylation reactor effluent stream into a lean solvent stream and an enriched alkylate product stream;

a first recycle line configured to recycle a first portion of the lean solvent stream to the absorber column; and a second recycle line configured to recycle a second portion of the lean solvent stream to the alkylation reactor.

2. The system of claim 1, wherein the solvent is isobutane.

3. The system of claim 1, wherein the olefin-containing stream is an off-gas from a fluid catalytic cracking (FCC) process.

4. The system of claim 1, further comprising an amine scrubber upstream of the absorber column, wherein the amine scrubber is configured to remove one or more contaminants selected from the group consisting of carbon dioxide and hydrogen sulfide from the olefin-containing stream.

5. The system of claim 1, further comprising a caustic contact vessel upstream of the absorber column, wherein the caustic contact vessel is configured to contact the olefin-containing stream with a caustic material to remove one or more contaminants selected from the group consisting of carbon dioxide and hydrogen sulfide from the olefin-containing stream.

6. The system of claim 1, wherein the alkylation reactor comprises a fixed catalyst bed comprising a solid acid alkylation catalyst.

* * * * *